US006482397B1

(12) United States Patent
Scott et al.

(10) Patent No.: US 6,482,397 B1
(45) Date of Patent: Nov. 19, 2002

(54) COLORING AGENT-CONTAINING SUNLESS TANNING COMPOSITIONS

(75) Inventors: John A. Scott, Succasunna, NJ (US); Eric M. Stroud, Oak Ridge, NJ (US); Alejandro V. Ortega, Jersey City, NJ (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 0 days.

(21) Appl. No.: 09/551,342

(22) Filed: Apr. 18, 2000

Related U.S. Application Data

(60) Provisional application No. 60/130,218, filed on Apr. 20, 1999.

(51) Int. Cl.$^7$ .......................... A61K 7/42; A61K 7/021; A61K 31/12; A61K 31/11
(52) U.S. Cl. .......................... 424/59; 424/63; 424/401; 574/675; 574/693; 574/844
(58) Field of Search .................. 424/401, 59, 63; 514/675, 693, 844

(56) References Cited

U.S. PATENT DOCUMENTS

| | | | |
|---|---|---|---|
| 3,940,477 A | 2/1976 | Vanlerberghe et al. | 424/59 |
| 3,975,294 A * | 8/1976 | Dumoulin | 252/354 |
| 4,434,154 A | 2/1984 | McShane | 424/60 |
| 5,232,688 A | 8/1993 | Ziegler et al. | 424/59 |
| 5,302,378 A | 4/1994 | Crotty et al. | 424/59 |
| 5,459,165 A * | 10/1995 | Bollens et al. | 514/768 |
| 5,514,367 A | 5/1996 | Lentini et al. | 424/59 |
| 5,514,437 A | 5/1996 | Tanner et al. | 424/63 |
| 5,569,460 A * | 10/1996 | Kurz et al. | 424/401 |
| 5,656,262 A | 8/1997 | Kurz et al. | 424/59 |
| 5,679,656 A | 10/1997 | Hansenne | 514/54 |
| 5,753,210 A | 5/1998 | McEleney et al. | 424/59 |
| 5,834,013 A * | 11/1998 | Ribier et al. | 424/450 |
| 6,214,322 B1 * | 4/2001 | Castro et al. | 424/59 |

FOREIGN PATENT DOCUMENTS

| | | | |
|---|---|---|---|
| EP | 0 386 680 A1 | * | 9/1990 |
| EP | 0 812 586 A1 | * | 12/1997 |
| WO | WO-98/23256 A1 | * | 6/1998 |
| WO | WO-98/44902 A1 | * | 10/1998 |

OTHER PUBLICATIONS

M. F. Bobin et al., *Journal of the Society of Cosmetic Chemists*, vol. 35, pp. 265–272 (1984).

* cited by examiner

*Primary Examiner*—Jose' G. Dees
*Assistant Examiner*—Marina Lamm
(74) *Attorney, Agent, or Firm*—Robert A. Franks

(57) ABSTRACT

This invention provides sunless-tanning compositions containing, in addition to a self tanning agent and a cosmetically acceptable carrier, a coloring agent, added to the compositions so as to enhance the uniformity of their application to the skin.

10 Claims, No Drawings

COLORING AGENT-CONTAINING SUNLESS TANNING COMPOSITIONS

CROSS-REFERENCE TO RELATED APPLICATION

This application claims benefit under 35 U.S.C. §119(e) from provisional application Serial No. 60/130,218 filed Apr. 20, 1999.

FIELD OF THE INVENTION

This invention relates to cosmetic compositions for topical application to human skin for the artificial tanning thereof, and more specifically, to such compositions having improved performance by the addition thereto of a coloring agent. This invention also relates to the use of such compositions to impart a tanned appearance to human skin.

BACKGROUND OF THE INVENTION

Direct exposure of human skin to natural sunlight is the most commonly used means of imparting a tan to the skin. Such exposure leads to tanning as a result of the darkening of preformed melanin in the skin, accelerated formation of new melanin and retention of melanin in the epidermis as a result of the retardation of keratinization therein. However, exposure to natural sunlight is frequently accompanied by several significant potential hazards, chief amongst which are the risk of sunburn, as well as the development of melanomas and other forms of skin cancer. Prolonged exposure to sunlight can also accelerate the natural aging process in the skin.

While some choose artificial sunlight as an alternative to exposure to natural sunlight, and as a potentially less risky means of obtaining a tan, this option too is not always suitable; hence, other options for skin tanning are desirable. One of these options, to which people are turning in increasing numbers, are the various "sunless tanning compositions" that can be used to impart a tan to human skin without the necessity of exposing the skin to natural, or artificial, sunlight. Such compositions contain, as their active agent, one or more of the available self tanning agents, including dihydroxyacetone ("DHA," 1,3-dihydroxy-2-propanone).

DHA, currently the most widely used of the self tanning agents, is believed to exert its effect through interactions between its hydroxy groups and the amino groups of amino acids and peptides naturally occurring in the hydrolipid pellicle and first layers of the stratum corneum of the skin. Such Maillard reactions are believed (see, e.g., Bobin et al., J. Soc. Cosmet. Chem. 35: 255 (1984)) to lead to formation of brown pigments in the skin, thereby giving it an appearance similar to that of a naturally obtained tan.

Although DHA-based, and other, self tanning agent-containing compositions are currently in widely accepted use, they do suffer from several attendant limitations, chief amongst which are a "streaky" tan, primarily resulting from the uneven application of the compositions to the skin of end users. Such unevenness primarily arises from the difficulty the users have in seeing the sunless tanning compositions once they have applied them to their skin, and hence, in ensuring that the compositions have been evenly applied. This invention addresses said limitation of presently available sunless tanning compositions with its inclusion in such compositions of coloring agents, the presence of which affords users the ability to more accurately assess where they have applied the compositions to their skin.

As described hereinabove, a variety of sunless-tanning agent formulations, including DHA-containing compositions, are currently known and in use. For example, Vanlerberghe and Rosenbaum (U.S. Pat. No. 3,940,477) describe the use of aminated gamma-dialdehydes in artificial skin tanning. U.S. Pat. No. 4,434,154 (McShane) describes a DHA-containing oil-in-water emulsion useful for both artificial tanning and ultraviolet screening. U.S. Pat. No. 5,232,688 (Ziegler and Crotty) add polyacrylamide to DHA-containing compositions for thickening purposes, as well as for improved low-odor performance. Crotty and Ziegler (U.S. Pat. No. 5,302,378) describe compositions containing DHA and an anionic silicon polyol, e.g., dimethicone polyol phosphate, added to the compositions to prevent streaking, and propylene glycol, added therein for improved color intensity. U.S. Pat. No. 5,514,367 (Lentini and Zecchino) adds cyclodextrins to DHA-containing sunless tanning compositions, for the purpose of composition stabilization, and odor reduction, during storage. Tanner and Robinson (U.S. Pat. No. 5,514,437) enhance the stability of DHA-containing compositions by adding a salt thereto. U.S. Pat. No. 5,656,262 (Kurz et al.) formulates DHA in sunless tanning compositions with ingredients intended to inhibit the production of formalin and formaldehyde therein. Kurz et al. (U.S. Pat. No. 5,569,640) add colorants, e.g., organic dyes such as eosin derivatives, to sunless tanning compositions, for the purpose of enhancing their self tanning performance. Hansenne et al. (U.S. Pat. No. 5,679,656) adds an alkylpolysaccharide/fatty alcohol mixture to its compositions, so as to enhance the stability of the DHA found therein.

However, none of these documents describe the solution to the "streaking" problem provided herein, namely, incorporation of caramel or a similarly pigmented compound into this invention's sunless tanning compositions. Kurz et al. (U.S. Pat. No. 5,569,460) describe compositions containing colorants intended to adhere to the skin, said colorants being organic dyes. However, the colorants of Kurz are used to color the skin to which its compositions are applied, thereby aiding in the artificial tanning process, and not to color the compositions themselves; hence, Kurz's compositions cannot be said to contain a composition coloring agent, as such agents are described herein. Moreover, such colorants as are described by Kurz compositions are employed in its compositions at concentrations below the effective amounts of the composition coloring agents of this invention. Crotty and Ziegler (U.S. Pat. No. 5,302,378) do attempt to solve the streaking problem, but their solution, use of an anionic silicone polymer, entails a completely approach from the compositions of this invention. Moreover, both U.S. Pat. No. 5,753,210 (McEleney et al.) and U.S. Pat. No. 5,753,210 rely upon pH-sensitive indicators to change color upon application to skin to show that their indicator-containing compositions have been applied to the skin.

SUMMARY OF THE INVENTION

This invention provides self tanning agent-containing cosmetic compositions suitable for imparting an artificial tan to human skin, the tan having an appearance similar to the effect caused by exposing the skin to natural or artificial sunlight. Said compositions contain: (a) an artificial tanning effective amount of a self tanning agent; (b) from greater than about 0.1% to about 5% of a composition coloring agent, e.g., caramel, grape extract or beta carotene, by weight of the composition; and, (c) a cosmetically acceptable carrier adapted for topical application to human skin.

The self tanning agent, preferably an alpha hydroxy aldehyde or ketone, is present in the compositions at artificial tanning effective amounts of from about 0.5% by weight to about 10% by weight of the composition. Most preferably, the tanning agent is DHA, and is present in this invention's compositions at concentrations of about 4% or about 5% by weight. The composition coloring agent, e.g., caramel, grape extract and beta carotene, is most desirably caramel, and is preferably present in the compositions at a concentration of about 0.8% by weight.

Accordingly, in the most preferred embodiments of this invention, the sunless tanning compositions provided herein comprise DHA, in amounts of about 4% or about 5% by weight, as the self tanning agent, and caramel, at a concentration of about 0.8% by weight, as the composition coloring agent.

Also provided herein is a method of imparting a tanned appearance to human skin in the absence of sunlight, said method comprising the application of the compositions provided herein to the skin.

DETAILED DESCRIPTION OF THE INVENTION

This invention provides sunless-tanning compositions, that is, compositions which, when applied to human skin, impart thereto an appearance similar to that achieved by exposing the skin to natural or artificial sunlight. Said sunless tanning compositions comprise, in addition to an artificial tanning effective amount of a self tanning agent, effective amounts of a composition coloring agent and a cosmetically acceptable carrier adapted for topical application to human skin.

Self tanning agents included in this invention's compositions are any of those agents generally accepted in the art for application to human skin, and which, when so applied, react therein with amino acids so as to form pigmented products. Such reactions give the skin a brown appearance similar to the color obtained upon exposing it to sunlight for periods of time sufficient to tan the skin. Suitable self tanning agents include, without limitation, alpha-hydroxy aldehydes and ketones, glyceraldehyde and related alcohol aldehydes, various indoles, imidazoles and derivatives thereof, and various approved pigmentation agents, e.g., methoxsalen and trioxsalen. Presently preferred herein as self tanning agents are the alpha-hydroxy aldehydes and ketones, i.e., compounds of the formula $R^1CH(OH)C(O)R^2$, wherein $R^1$ is H, $CH_2OH$, $CH(OH)CH_2OH$, $CH(OH)C(O)H$, $CH(OCH_3)C(O)H$, $CH(NH2)C(O)H$ and $CH(NH\text{-}Phenyl)C(O)H$, and $R_2$ is H or $CH_2OH$.

Most preferably, the self tanning agent included in this invention's compositions is dihydroxyacetone ("DHA"), i.e., $CH_2OHC(O)CH_2OH$. Other suitable self tanning agents include, without limitation, methyl glyoxal, glycerol aldehyde, erythrulose, alloxan, 2,3-dihydroxysuccindialdehyde, 2,3-dimethoxysuccindialdehyde, 2-amino-3-hydroxy-succindialdehyde and 2-benzylamino-3-hydroxysuccindialdehyde.

Such self tanning agents are present in this invention's compositions at concentrations which establish therein "artificial tanning effective amounts" of the agents. Such effective amounts are amounts of the agents which, when applied to human skin, impart an appearance thereto similar to that obtained by exposing the skin to natural or artificial sunlight for a period of time sufficient to tan the skin. Ordinarily skilled artisans given the description of this invention provided herein and their own knowledge are well able to determine appropriate artificial tanning effective amounts of various self tanning agents to incorporate in sunless tanning compositions, using well known and readily practiced means, e.g., application of varying amounts of particular agents to the skin of volunteer subjects. Typically, but not necessarily, artificial tanning effective amounts of self tanning agents in this invention's compositions are from about 0.5% of the agent by weight of the composition to about 10% by weight. Most preferably, with the self tanning agent being dihydroxyacetone, compositions provided herein contain DHA at concentrations of about 4% or about 5% by weight.

This invention's compositions also comprise a "composition coloring agent," that is, a cosmetically acceptable pigmented compound capable of affording sunless tanning compositions an appearance sufficiently observable by the compositions' end users so as to allow them to determine where they have applied the compositions to their skin, while not also having an adverse effect on the appearance of the tanned skin resulting from the sunless tanning process. Composition coloring agents include, for example and without limitation, caramel, grape extract and beta carotene, with caramel presently being the preferred agent for inclusion in this invention's compositions.

Composition coloring agents are included in the compositions in "effective amounts," that is, in amounts sufficient for composition coloration without interfering with the sunless tanning process. Such amounts are from greater than about 0.1% by weight of the composition to about 5% by weight, more preferably, bout 0.8% by weight of the composition.

Accordingly, in the most preferred embodiments of this invention, the compositions provided herein comprise DHA as a self tanning agent, at a concentration of about 4% or about 5% by weight, and caramel as a composition coloring agent, at a concentration of about 0.8% by weight.

Compositions of this invention comprise, in addition to said self tanning and coloring agents, a "cosmetically acceptable carrier adapted for topical application to human skin," which is any of those media accepted in the art for dermatological use in connection with human skin. Such carriers are based on a vehicle that can deliver the active agent to the skin such that it is capable of being effective thereon. The compositions can also contain a number of additional ingredients, useful for a variety of purposes therein, e.g., to stabilize the active agent and enhance its activity, to preserve the compositions' integrity, and to enable the compositions to be formulated according to the means by which they are to be applied.

Additional ingredients for incorporation in this invention's sunless tanning compositions are selected from amongst a variety of such additives, including, without limitation the following. Acidifying agents, e.g. acetic acid, glacial acetic acid and maleic acid, and alkalizing agents, e.g., potassium hydroxide, sodium borate, sodium carbonate and sodium carbonate, are added to the compositions for pH-adjustment purposes. Aerosol propellants, e.g., acceptable halogenated hydrocarbons (such as dichlorodifluoromethane, dichlorotetrafluoroethane and trichloromonofluoromethane), nitrogen and volatile hydrocarbons (such as butane, propane and isobutane), are used when the composition is to be applied, under pressure, as a spray.

Antimicrobial agents and preservatives inhibit microbial growth in the compositions, and can also be used to treat infected, or potentially infected, areas of skin. Suitable agents and preservatives include, without limitation: benzalkonium chloride, benzoic acid, benzyl alcohol, butylparaben, chlorbutanol, ethyl paraben, methyl paraben, parahydroxybenzoic acid alkyl esters, phenylethyl alcohol, phenyl mercuric acetate, potassium sorbate, proprionate salts, propylparaben, sodium benzoate, sodium dehydroacetate and sorbic acid.

Antioxidants, e.g., ascorbyl palmitate, butylated hydroxytoluene (BHT), hypophosphoric acid, potassium or sodium metabisulfite, and tocopherols/tocopherol esters, prevent oxidative damage to the compositions' other ingredients. Buffering agents, e.g., calcium acetate, potassium metaphosphate, potassium phosphate monobasic and tartaric acid, maintain composition pH. Chelating agents, e.g., EDTA, maintain the compositions' ionic strength and remove destructive ions therefrom.

Dermatologically active agents, e.g., wound healing agents (such as panthenol, phenol and tetracycline hydrochloride, anti-inflammatory agents (such as hydrocortisone, dexamethisone, and methylprednisolone), retinoids (e.g., retinol, tretinoin and arotinopid), antihistamines (such as diphenhydramine, terfenadine and loratadine), topical analgesics and anesthetics (such as benzocaine, camphor, dibucaine, lidocaine and methyl salicylate), and vitamins/vitalnin derivatives, are added to the compositions for a variety of purposes, including for disease treatment, nutrition and pain or inflammation relief.

Emollients, e.g., hydrocarbon oils and waxes (such as mineral oil, petrolatum and microcrystalline wax), triglyceride esters (such as of castor oil, cocoa butter and cottonseed oil), acetylated monoglycerides, ethoxylated glycerides, $C_{10}$–$C_{20}$ fatty acids and alcohols (such as myristic, palmitic and stearic acids or alcohols), alkyl (e.g., $C_1$–$C_4$) esters of $C_{10}$–$C_{20}$ fatty acids, fatty alcohol ethers, lanolin and derivatives thereof (such as lanolin, lanolin oil and lanolin wax), polyhydric alcohol esters (such as ethylene glycol, polyethylene glycol and polypropylene glycol mono- and di-fatty acid esters), wax esters (such as beeswax) and derivatives thereof, vegetable waxes (such as carnuba wax), phospholipids (such as phosphatidylcholine) and derivatives thereof, and sterols (e.g., cholesterol) and derivatives thereof), soften and smooth skin to which the compositions of this invention have been applied.

Emulsifying agents, e.g., polyethylene glycols of MW 200–6000, sorbitol, hydrophilic wax esters, cetostearyl alcohol, mono- and diglycerides, glyceryl monostearate, polyethylene glycol monostearate, mixed mono- and distearic esters of ethylene glycol and polyoxyethylene glycol, and propyleneglycol monostearate, enable the composition of this invention to be prepared as an emulsion, preferably, an oil-in-water emulsion. Humectants, e.g., sorbitol, glycerin, glyceryth 5 lactate, propylene glycol and D-panthenol, promote retention of moisture on the skin to which compositions of this invention have been applied. Perfumes and fragrances, e.g., menthol, camphor and eucalyptus oil enhance the appeal of the compositions to their end users.

Sequestering agents, such as those comprising cyclodextrins, are known to enhance the stability of DHA and other self tanning agents. Solvents, e.g., alcohols, oils and purified water, solubilize other components of the composition. Sugars used with sunless tanning compositions to improve results include various mono-, di- and polysaccharides. Sunscreen agents, e.g., 2-ethylhexyl-N,N-dimethyl-p-aminobenzoate, oxybenzone and p-aminobenzoic acid, reduce the amount of ultraviolet radiation impinging upon the skin. Surfactants, useful as wetting, emulsifying, dispersing, penetrating and antifoaming agents, include laureth 4 and 9, nonoxynol 4, 9, 10, 15 and 30, polyoxyl 8, 40 and 50 stearate, and polysorbate 20, 40, 60, 80 and 85.

Various other types of additives, e.g., dispersing and suspending agents, excipients, ointment bases, penetration enhancers, preservatives, stabilizers and stiffening agents, can also be incorporated into this invention's compositions. Moreover, any one compound can have a number of different properties, and can be assigned to more than one of the above-identified categories. For example, xanthan gum has both stabilizing and emulsifying properties, and dimethicone has both skin protecting and emollient properties.

Those of ordinarily skill in the cosmetic arts are well able to determine the types and amounts of additives to be included in sunless tanning compositions, and have a variety of sources to consult for this purpose (e.g., the CTFA International Ingredient Dictionary 4th ed., The Cosmetic, Toiletry and Fragrance Association, Inc., Washington, D.C. (1997), the contents of which are incorporated herein by reference).

Sunless tanning compositions provided herein can comprise one or more of these various types of ingredients; presently preferred additives include the following. Ethoxydiglycol is included in the compositions as a solvent, typically at a concentration of from about 1% by weight of the compositions to about 10% by weight; more preferably, ethoxydiglycol is included in the compositions at a concentration of about 5% by weight. Inositol is, for example, a dermatologically active agent having nutritive properties typically included at concentrations of about 0.5% to 5% by weight and more preferably, at about 2% by weight. Xanthan gum is, for example, a stabilizing and emulsifying agent, typically included at concentrations of about 0.1% to 1% by weight, and more preferably, at about 0.3% by weight. Cetyl hydroxyethylcellulose is, for example, an emulsifier, stabilizer and thickener, typically included at concentrations of about 0.1% to 1% by weight, and more preferably, at about 0.3% by weight. Cetyl and stearyl alcohols are, for example, emollients, emulsion modifying agents and stiffening agents, typically included at concentrations of about 0.5% to 5% by weight, and more preferably, at about 2% by weight. Octyl palmitate is, for example, a solvent typically included at concentrations of about 0.5% to 5% by weight, and more preferably, at about 2% by weight. Glucam P-20 distearate is, for example, an emulsifier typically included at concentrations of about 0.5% to about 5% by weight, and more preferably, at about 2% by weight. Steareth-20 is, for example, an emulsifier typically included at concentrations of about 0.5% to 5% by weight, and more preferably, at about 1% by weight. Dirnethicone is, for example, a skin protectant and emollient typically included at concentrations of about 0.5% to 5% by weight, and more preferably, at about 1% by weight. Polysorbate 60 is, for example, an emulsifying agent typically included at concentrations of about 0.5% to about 5% by weight, and more preferably, at about 1% by weight. Polyderm PPI-SI-WI® (polydimetylsiloxane-polyethylene glycol/isophorone diisocyanate copolymer is, for example, a film-forming agent typically included at concentrations of about 0.5% to about 5% by weight, and more preferably, at about 1% by weight. Arlacel® (glyceryl stearate and PEG-100 stearate) is, for example, an emulsifying agent typically included at concentrations of about 0.10% to 1.0% by weight, and more preferably, at about 0.25% by weight. Actiplex 335 Lipo OP® (a combination of lanolin, palm oil, cocoa butter, aloe eucalyptus oil, apricot and matricaria in an octyl palmitate carrier) is, for example, an emollient, moisturizer, skin softener and fragrance typically included at concentrations of about 0.05% to about 0.5% by weight, and more preferably, at about 0.1% by weight. Tocopheryl acetate is, for example, an antioxidant typically included at concentrations of about 0.05% to 0.5% by weight, and more preferably, at about 0.1% by weight. Nipaguard MPA® (a combination of benzyl alcohol, butyl paraben, methyl paraben and propylparaben) is, for example, an antimicrobial agent and preservative typically included at concentrations of about 0.1% to about 1% by weight, and more preferably, at about 0.6% by weight. Panthenol (50% aqueous) is, for example, a wound healing agent typically included at concentrations of about 0.1% to 1% by weight, and more preferably, at about 0.4% by weight. Sorbic acid is, for example, an antimicrobial agent and preservative typically included at concentrations of about 0.01% to 0.1% by weight, and more preferably, at about 0.05% by weight. Sodium metabisulfite is, for example, a reducing or antioxidizing agent typically included at concentrations of about 0.010% to 0.100% by weight, and more preferably, at about 0.025% by weight. Moreover, additional ingredients, e.g., fragrance #433016 at a concentration of about 0.1% by weight, can also be incorporated into this invention's sunless tanning compositions.

The specific formulations of preferred embodiments of this invention are set forth hereinbelow in the Examples section. However, those of ordinary skill in the arts will readily understand that such specific formulations are as set forth in the examples are merely illustrative of this invention's compositions, as defined in the claims which follow thereafter.

Compositions of this invention are formulated for application to skin in a number of different ways. Compositions intended for application as sprays or mists, for example, are formulated as aerosols by inclusion therein of aerosol propellants; the compositions can also be applied as sprays and mists without aerosolization, generally using mechanical dispersion. Compositions can also be applied as milks, creams, gels or lotions, and then rubbed into the skin; such compositions can be aqueous solutions comprising the self tanning agent in which a suitable viscosity has been achieved, but more likely are emulsions, preferably oil-in-water emulsions, containing the agent. Such emulsions are established by the combination of aqueous and organic solvents with emulsifying agents and various additional ingredients intended to stabilize the coexistence of the emulsion's continuous and discontinuous phases. The amount of water contained within the compositions varies according to the desired consistency of the final product., i.e., free- or thick-flowing liquids, lotions, creams, gels or sticks.

Compositions of this invention are prepared using methods well known to those of ordinary skill in the art. Examples of methods of composition preparation are provided hereinbelow, and incorporated herein by reference. However, those of ordinary skill in the art will readily understand that such specific methods as are set forth hereinbelow are merely exemplary, and that any of the methods accepted in the art for preparing cosmetic compositions are suitable for use herein.

Further provided herein is a method of imparting a tanned appearance to human skin, said method comprising applying compositions of this invention to the skin. Said compositions are applied in amounts dependent upon a number of factors, including, without limitation, the end users' skin tone, the means of application and the concentration of self tanning agent in the compositions. Accordingly, the amount of the composition applied generally depends to a significant, but not exclusive, degree upon the end users. However, the amounts applied by a particular end user of this invention's compositions is less than the amount of known sunless tanning compositions that would be applied by the same user, due to the inclusion in this invention's formulations of a composition coloring agent. As described above, the incorporation of such agents into this invention's compositions allows their end users to better assess where the compositions have been applied to their skin, and hence, to feel the need to apply lesser amounts of the compositions in order to obtain adequate skin coverage and an evenly tanned appearance.

Subsequent to their application, this invention's compositions are left remaining on the skin for periods of time dependent upon a number of factors, including, without limitation, the degree of tanned appearance desired by the end users, the concentration of self-tanning agent in the compositions, and the degree to which the compositions are rubbed into the skin, in the case of creams, lotions, gels and the like, or the degree to which the skin is otherwise induced to absorb the self tanning agent. Such factors again indicate that these time periods are dependent to a largely, but not exclusive, degree upon individual end users.

This invention's compositions are prepared by any of the methods known in the cosmetic arts for preparing sunless tanning compositions. For example and as set forth hereinbelow, but without limitation, the individual hydrophilic and lipophilic components of the compositions are brought together as distinct phases in a reaction vessel, and then mixed using standard techniques, e.g., turbine agitation, and generally available equipment, e.g., stainless steel vessels and Lee mixers.

EXAMPLE 1

Sunless Tanning Composition for Producing a Dark Tan

The individual components of the sunless tanning composition, identified specifically in Table 1 (see below), were brought together in three phases, i.e., three different groups of ingredients (A, B and C) were added to the vessel in which the formulation was prepared. The order of addition of each of the three groups to the vessel in which the formulation was made was group A, then group B and following that, group C. The components were mixed using standard techniques and equipment, e.g., turbine agitation with a Lee mixer in a stainless steel vessel, Processing conditions included a temperature of about 77° C. for the mixing of groups A and B, and a temperature of about 40° C. for the addition thereto of group C.

TABLE 1

| Component | Ingredient Description | Weight Percentage Concentration |
|---|---|---|
| A | Water | 65.0 |
| A | Ethoxydiglycol | 5.0 |
| A | Inositol | 2.0 |
| A | Caramel | 0.8 |
| A | Xanthan gum | 0.3 |
| A | Cetyl hydroxyethylcellulose | 0.3 |
| B | Cetyl alcohol | 2.0 |
| B | Stearyl alcohol | 2.0 |
| B | Octyl palmitate | 2.0 |
| B | Glucam P-20 distearate[a] | 2.0 |

TABLE 1-continued

| Component | Ingredient Description | Weight Percentage Concentration |
|---|---|---|
| B | Steareth-20 | 1.0 |
| B | Dimethicone | 1.0 |
| B | Polysorbate 60 | 1.0 |
| B | Polyderm PPI-SI-WI[b] | 1.0 |
| B | Arlacel 165[c] | 0.25 |
| B | Actiplex 335 Lipo OP[d] | 0.1 |
| B | Tocopheryl acetate | 0.1 |
| C | Water | 8.975 |
| C | Dihydroxyacetone | 4.0 |
| C | Nipaguard MPA[e] | 0.6 |
| C | Panthenol, 50% aqueous | 0.4 |
| C | Sorbic acid | 0.05 |
| C | Sodium metabisulfite | 0.025 |
| C | Fragrance #433016 | 0.1 |

[a]PPG-20 methyl glucose ether distearate;
[b]polydimethylsiloxanepolyethylene glycol/isophorone diisocyanate copolymer;
[c]glyceryl stearate and PEG-100 stearate;
[d]lanolin, palm oil, cocoa butter, aloe, eucalyptus, apricot and matricaria in an octyl palmitate carrier;
[e]benzyl alcohol, methyl-, propyl- and butylparaben.

EXAMPLE 2

Sunless Tanning Composition for Producing a Deep Dark Tan

The individual components of the sunless tanning composition, identified specifically in Table 2 (see below), were brought together in three phases, i.e., three different groups of ingredients (A, B and C) were added to the vessel in which the formulation was prepared. The order of addition of each of the three groups to the vessel in which the formulation was made was group A, then group B and following that, group C. The components were mixed using standard techniques and equipment, e.g., turbine agitation with a Lee mixer in a stainless steel vessel, Processing conditions included a temperature of about 77° C. for the mixing of groups A and B, and a temperature of about 40° C. for the addition thereto of group C.

TABLE 2

| Component | Ingredient Description | Weight Percentage Concentration |
|---|---|---|
| A | Water | 65.0 |
| A | Ethoxydiglycol | 5.0 |
| A | Inositol | 2.0 |
| A | Caramel | 0.8 |
| A | Xanthan gum | 0.3 |
| A | Cetyl hydroxyethylcellulose | 0.3 |
| B | Cetyl alcohol | 2.0 |
| B | Stearyl alcohol | 2.0 |
| B | Octyl palmitate | 2.0 |
| B | Glucam P-20 distearate[a] | 2.0 |
| B | Steareth-20 | 1.0 |
| B | Dimethicone | 1.0 |
| B | Polysorbate 60 | 1.0 |
| B | Polyderm PPI-SI-WI[b] | 1.0 |
| B | Arlacel 165[c] | 0.25 |
| B | Actiplex 335 Lipo OP[d] | 0.1 |
| B | Tocopheryl acetate | 0.1 |
| C | Water | 8.975 |
| C | Dihydroxyacetone | 4.0 |
| C | Nipaguard MPA[e] | 0.6 |
| C | Panthenol, 50% aqueous | 0.4 |
| C | Sorbic acid | 0.05 |
| C | Sodium metabisulfite | 0.025 |
| C | Fragrance #433016 | 0.1 |

[a]PPG-20 methyl glucose ether distearate;
[b]polydimethylsiloxanepolyethylene glycol/isophorone diisocyanate copolymer;
[c]glyceryl stearate and PEG-100 stearate;
[d]lanolin, palm oil, cocoa butter, aloe, eucalyptus, apricot and matricaria in an octyl palmitate carrier;
[e]benzyl alcohol, methyl-, propyl- and butylparaben.

What is claimed is:

1. A composition comprising: (a) an artificial tanning effective amount of a self tanning agent; (b) a composition coloring agent at a concentration of about 0.8% by weight of the composition; and (c) a cosmetically acceptable carrier adapted for topical application to human skin.

2. The composition of claim 1, wherein the self tanning agent is an alpha-hydroxy aldehyde or ketone.

3. The composition of claim 2, wherein the self tanning agent is dihydroxyacetone ("DHA").

4. The composition of claim 1, wherein artificial tanning effective amount of the self tanning agent is from about 0.5% by weight of the composition to about 10% by weight.

5. The composition of claim 1 wherein the self tanning agent comprises dihydroxyacetone, present at about 4% by weight or about 5% by weight.

6. The composition of claim 1, wherein the composition coloring agent is selected from the group consisting of caramel, grape extract and beta carotene.

7. The composition of claim 6, wherein the coloring agent is caramel.

8. The composition of claim 1, wherein the coloring agent comprises caramel.

9. The composition of claim 1, wherein the coloring agent comprises caramel and the self tanning agent comprises about 4% by weight or about 5% by weight dihydroxyacetone.

10. A method of imparting a tanned appearance to human skin comprising applying the composition of claim 1 to the skin.

* * * * *